United States Patent
Henriksen et al.

(10) Patent No.: US 6,509,004 B1
(45) Date of Patent: Jan. 21, 2003

(54) PROCESS FOR PREPARING CONTRAST AGENTS

(75) Inventors: Ingrid Henriksen, Oslo; Vera Kasparkova, Slependen; Arnfinn Andersen; Anne Kjersti Fahlvik, both of Oslo; Liv Ingrid Odegardstuen, Leirsund, all of (NO)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/506,682

(22) Filed: Feb. 18, 2000

Related U.S. Application Data

(63) Continuation of application No. PCT/GB98/02490, filed on Aug. 19, 1998.
(60) Provisional application No. 60/064,310, filed on Nov. 5, 1997.

(30) Foreign Application Priority Data

Aug. 19, 1997 (GB) .............................. 9717542

(51) Int. Cl.$^7$ ............................ A61B 8/00; B01F 17/00
(52) U.S. Cl. ......................... 424/9.52; 516/11; 516/77
(58) Field of Search ............... 424/9.3, 9.323, 424/9.36, 489; 516/11, 77; 428/402

(56) References Cited

U.S. PATENT DOCUMENTS

| | | | |
|---|---|---|---|
| 4,642,903 A | 2/1987 | Davies | 34/284 |
| 4,857,319 A | 8/1989 | Crowe et al. | 424/94.1 |
| 5,741,478 A | * 4/1998 | Osborne et al. | 424/9.52 |
| 6,120,751 A | * 9/2000 | Unger | 424/9.51 |

FOREIGN PATENT DOCUMENTS

| | | | | |
|---|---|---|---|---|
| DE | 195 10 690 A | 9/1996 | | |
| DE | 196 11 769 A | 9/1997 | | |
| WO | WO 9401140 A | 1/1994 | | |
| WO | WO 94 09829 A | 5/1994 | | |
| WO | WO 96/15814 | * 5/1996 | ........... | A61K/49/04 |
| WO | WO 96 26746 A | 9/1996 | | |
| WO | WO 97/12551 | * 4/1997 | ............ | A61B/8/00 |
| WO | WO 97 29782 A | 8/1997 | | |
| WO | WO 97 29783 A | 8/1997 | | |

OTHER PUBLICATIONS

Mosharraf M. et al., "Effect of Calcium Ions on the Surface Charge and Aggregation of Phosphatidylcholine Liposomes" Journal Of Drug Targeting, 1995, XP002088453.

Wilschut et al., "Modulation of Membrane Fusion by Membrane Fluidity: Temperature Dependence of Divalent Cation Induced Fusion of Phosphatidylserine Vesicles", Biochemistry, 1985, XP000676613.

* cited by examiner

*Primary Examiner*—Michael G. Hartley
(74) *Attorney, Agent, or Firm*—Royal N. Ronning, Jr.; Robert F. Chisholm

(57) ABSTRACT

The invention provides a process for the preparation of a pharmaceutical composition comprising an aqueous dispersion of gas-containing vesicles the membranes whereof comprise an amphiphilic membrane-forming material, said process comprising: (i) generating a liquid dispersion of gas-containing vesicles from a mixture comprising an amphiphilic membrane forming material; (ii) lyophilizing a liquid dispersion of said gas-containing vesicles; (iii) reconstituting the lyophilized product of step (ii) with a sterile aqueous liquid to produce an aqueous dispersion of gas-containing vesicles; and (iv) treating the aqueous dispersion product of step (iii) or the lyophilized product of step (ii) to produce a substantially aggregate-free sterile aqueous dispersion of gas-containing vesicles.

10 Claims, 1 Drawing Sheet

PROCESS FOR PREPARING CONTRAST AGENTS

This application is a continuation of pending international application number PCT/GB98/02490 filed Aug. 19, 1998 (of which the entire disclosure of the pending, prior application is hereby incorporated by reference), which itself is a continuation-in-part of U.S. provisional application No. 60/064,310 filed Nov. 15, 1997.

This invention relates to improvements in and relating to compositions, particularly pharmaceutical compositions, containing gas-containing vesicles, for example for use as contrast agents in ultrasound imaging.

The use of compositions containing gas-containing vesicles (e.g. microballoons, liposomes, etc) as echogenic contrast agents in ultrasound imaging has been widely proposed in recent years and several such compositions are available or under clinical trial.

Several different types of vesicle membrane have been proposed, e.g. synthetic polymer, protein, phospholipid, etc. The present invention is concerned with vesicles having an amphiphilic membrane forming material, for example a surfactant or a lipid, in particular a phospholipid and most particularly one or more phospholipids having negatively charged groups, especially those having an overall negative charge, such as phosphatidylserines and phosphatidic acids.

Whilst gas-containing vesicles can readily be prepared from such amphiphilic membrane forming materials, for example by shaking, sonicating or rotor-stator mixing a gas and a liquid medium containing the membrane forming material, we have found that where the resulting composition is lyophilized there is a small degree of vesicle aggregation, agglomeration, flocculation or fusion following reconstitution of the lyophilisate with aqueous media.

Viewed from one aspect therefore the invention provides a process for the preparation of a pharmaceutical composition comprising an aqueous dispersion of gas-containing vesicles the membranes whereof comprise an amphiphilic membrane forming material, said process comprising:

(i) generating a liquid dispersion of gas-containing vesicles from a mixture comprising an amphiphilic membrane forming material;

(ii) lyophilizing a liquid dispersion of said gas-containing vesicles;

(iii) reconstituting the lyophilized product of step (ii) with a sterile aqueous liquid to produce an aqueous dispersion of gas-containing vesicles; and (iv) treating the aqueous dispersion product of step (i) or step (iii) or the lyophilized product of step (ii) to produce a substantially aggregate-free sterile aqueous dispersion of gas-containing vesicles.

Preferred amphiphilic membrane-forming materials include materials having negative charges, particularly preferably those having an overall negative charge. Yet more particularly preferred amphiphilic membrane-forming materials are those comprising serine groups, and particularly phospholipids comprising serine groups e.g. phosphatidyl serine.

The terms aggregate, agglomerate, and flocculate refer to associations of individual intact vesicles. The process of the invention reduces one or more of these effects and the term aggregate (or aggregation) is thus used herein to refer to one or more of these associations.

The treatment of step (iv) may take the form of the use in the reconstitution step (iii) of a sterile aqueous liquid meeting particular criteria or alternatively or additionally it may involve chemical and/or mechanical treatment of the dispersion in step (i) or the reconstituted aqueous dispersions.

The tendency of vesicles formed using amphiphilic membrane-forming materials having negatively charged groups to agglomerate in a suspension medium containing multivalent metal cations appears to be increasingly severe as the vesicle content within the suspension medium is reduced. Increasing the phospholipid content of the amphiphilic membrane-forming materials of the membranes of the vesicles, or increasing the amount of membrane-forming materials, or increasing the phospholipid surface area of the membrane-forming materials, appears to reduce the tendency of individual intact vesicles to agglomerate. Such increases in phospholipid content or surface area can be achieved for example by adjusting accordingly the components used in the manufacture of the vesicles, or by adjusting the manufacturing process so as to increase the amount of phospholipid not incorporated in the microbubbles.

Moreover, the time taken between the filling of the sample vials and the freezing of the samples (i.e. the floating time) has been found to be the most important factor affecting the amount of agglomeration of vesicles. For example, it has been shown that immediate freezing results in a considerable reduction in agglomerates formed and that this reduction is independent of any adjustments made to the process and composition of the vesicles. Thus, preferably the time from generating the liquid dispersion of vesicles and the subsequent flotation and fractionation of the vesicles to the freeze drying or lyophilising of the liquid dispersion is minimised.

An increase in the phospholipid content or surface area can also be achieved by adjusting the manufacturing process so as to induce a shift downwards in the particle size distribution, to increase the available surface of phospholipids by way of increasing the number concentration of microbubbles present.

Such increases in phospholipid content as discussed above have not only been shown to correlate positively with reduced aggregation of vesicles on reconstitution, but also correlate positively with a reduced sensitivity to aggregation induced by calcium ions in the reconstitution medium (i.e. an increased calcium tolerance). This correlation of increased calcium tolerance with increased phospholipid content is shown in FIG. 2. Calcium tolerance is defined as the lowest ion concentration to produce visible or microscopic agglomeration.

Preferably, the ratio of the total molar concentration in the aqueous suspension medium of non-chelated Al, Ba, Mg, Ca and Zn (and particularly preferably also Fe) to the molar concentration of the amphiphilic membrane-forming materials having negatively charged groups is less than 1:2, particularly less than 1:2.5, more preferably less than 1:3 and most preferably less than 1.6.

Thus viewed from a further aspect the invention provides a pharmaceutical composition comprising an aqueous dispersion of gas-containing vesicles the membranes whereof comprise an amphiphilic material (e.g. a phospholipid) having negatively charged groups, wherein the ratio of the total molar concentration in the aqueous dispersion of non-chelated Al, Ba, Mg, Ca and Zn (and particularly preferably also Fe) ions to the molar concentration of the amphiphilic membrane-forming material having negatively charged groups is less than 1:2, particularly less than 1:2.5, more preferably less than 1:3 and most preferably less than 1:6.

Another means of reducing aggregate formation is to reconstitute the lyophilizate with an aqueous liquid, such as sterile water, which has a total concentration of less than 100 $\mu$M of non-chelated Al, Ba, Ca, Mg and Zn ions, preferably a total of less than 50 $\mu$M, especially less than 47 $\mu$M, more especially less than 45 μM, more especially less than 40 μM, more especially less than 35 μm, more especially less than 30 μm and most especially less than 25 μM. Particularly preferably, these total concentration limits apply for other multivalent counter ions to the amphiphilic membrane forming material, for example Fe ions. Most preferably the sum of Mg and Ca ions has a concentration of less than 50 AM, especially the sum of Mg and Ca and Al ions is less than 30 μm. Preferably, the concentration of non-chelated individual divalent ions such as Mg, Ca, Ba and Zn is less than 30 μM and that of unchelated trivalent ions such as Al is less than 30 μM.

Viewed from a further aspect therefore, the invention provides a pharmaceutical composition, preferably for parenteral administration, comprising a dispersion of gas-containing vesicles in a sterile aqueous medium, wherein the total concentration of non-chelated Al, Ba, Ca, Mq and Zn ions in the resulting aqueous dispersion is Less than 100 μM, preferably less than 50 μM, especially less than 47 μM, more especially less than 45 μM, more especially less than 40 μm, more especially less than 35 μm, even more especially less than 30 μM and most especially less than 25 μM. Most preferably the sum of Mg and Ca ions has a concentration of less than 50 μM, especially the sum of Mg and Ca and Al ions is less than 30 μM. Again the concentrations of individual non-chelated Mg, Ca, Ba and Zn ions is preferably less than 30 μM and the concentration of non-chelated Al ions is preferably less than 30 μM.

By non-chelated it is meant that the ions are free or are bound sufficiently weakly as to be scavengable by EDTA.

Water available commercially for pharmaceuticals, even sterile water or water for injections does not necessarily fulfil these metal ion concentration criteria.

Accordingly, viewed from a yet further aspect the invention provides the use, for the manufacture of a pharmaceutical composition containing gas-containing vesicles (e.g. a composition for use as a contrast medium in a method of diagnosis involving a diagnostic imaging procedure) by admixture to a gas-filled vesicle containing material of a sterile aqueous liquid (preferably water) either wherein the ratio of the total molar concentration in the resulting aqueous dispersion of non-chelated Al, Ba, Mg, Ca and Zn (and particularly preferably also Fe) to the molar concentration of the amphiphilic membrane-forming materials having negatively charged groups is less than 1:2, particularly less than 1:2.5, more preferably less than 1:3 and most preferably less than 1:6, or wherein the total concentration of non-chelated Al, Mg, Ca, Ba and Zn ions is less than 100 μM, preferably less than 50 μM, etc.

Viewed from a still further aspect the invention provides a process for the production of an aqueous dispersion of gas-containing vesicles, said process comprising:

(i) obtaining a sterile aqueous liquid;
(ii) determining the total concentration of non-chelated Al, Ba, Mg, Ca and Zn in said liquid;
(iii) adding said liquid to a material containing gas-containing vesicles so that the ratio of the total molar concentration in the resulting aqueous dispersion of non-chelated Al, Ba, Mg, Ca and Zn ions to the molar concentration of the amphiphilic membrane forming material of said vesicles is less than 1:2, particularly less than 1:2.5, more preferably less than 1:3 and most preferably less than 1:6.

Viewed from a yet further aspect the invention provides a process for the production of an aqueous dispersion of gas-containing vesicles, said process comprising:

(i) obtaining a sterile aqueous liquid;
(ii) determining whether said liquid has a total concentration of non-chelated Al, Ba, Mg, Ca and Zn ions of less than 100 μM, preferably less than 50 μm, etc;
(iii) adding said liquid determined to have a total concentration of non-chelated Al, Ba, Mg, Ca and Zn ions of less than 100 μM, preferably less than 50 μm, etc., or treated to have a total concentration of non-chelated Al, Ba, Mg, Ca and Zn ions of less than 100 μM, preferably less than 50 μm, etc., to a material containing gas-containing vesicles, e.g. a lyophilizate.

The free di- or trivalent metal ion concentration in water may be reduced by addition of a chelating agent, e.g. citrate, EDTA, desferrioxamine or any other known chelating agent. In particular, the chelating agent used is a calcium or magnesium chelating agent, e.g. an aminopolycarboxylic acid or other polybasic acid such as EDTA, DTPA, DTPA-BMA, DOTA, DO3A, TMT, PLED, DPDP or EGTA, most preferably EDTA. Examples of suitable chelating agents may be found in the literature, especially the published patent applications of Nycomed, Salutar, Sterling Winthrop, Schering, Bracco, Squibb, Guerbet and Mallinckrodt, relating to diagnostic contrast agents, in particular for MR and nuclear imaging.

Thus aqueous reconstitution media which do not meet the above criteria may be used according to the invention where a chelating agent, preferably a physiologically tolerable chelating agent, is added to the reconstitution fluid before, during or after it is contacted with the lyophilizate. The quantity of chelating agent used will desirably be such as to cause the concentrations of non-chelated di- or trivalent metal ions to fall below the limits specified above. Typically, for commercially available "pure" water, the chelating agent may be added at concentrations of 5 to 1000 μM, e.g. 10 to 500 μM, especially 30 to 100 μM.

Chelating agents are frequently acids which are relatively insoluble in their free acid form. Accordingly, it may be desirable to use salts of chelating agents in which the counterion is monovalent and physiologically tolerable, e.g. organic amine, ammonium or alkali metal (e.g. sodium) salts.

The chelating agent may be included in the vesicle containing composition prior to lyophilization, it may be added to the reconstitution medium before reconstitution or it may be added to the reconstituted dispersion.

While sterile water is preferably used for reconstitution of the lyophilized product, certain solutes may also be present, for example chelating agents, osmolality adjusting agents, and pH regulators. In this regard, it is clearly not desirable to use materials which introduce non-chelated multivalent metal ions. Suitable osmolality adjusting agents include sugars such as sucrose, glucose, maltose, glycerol, mannitol and sorbitol. Suitable buffers include Tris and other organic amine based buffer systems. Preferably the pH of the suspension medium will be maintained above 4.5, e.g. 6 to 9, preferably about 7.

Alternatively or additionally to the control of multivalent metal ion concentration, or the ratio of the multivalent metal ion concentration to the concentration of the amphiphilic membrane-forming material, agglomeration may be reduced or substantially removed physically (e.g. by filtration), and/or by subjecting the reconstituted medium to mechanical stress, e.g. by vigorous shaking, sonication, or extrusion, e.g. by filtration or passage through limited diameter apertures, for example through tubes of 1 mm or less internal diameter. Such mechanical stress which involves exposure to substantial shear forces due to turbulence is clearly differentiated from the use of gentle manual shaking to disperse the lyophilizate in the reconstitution medium, ie. shaking which would expose the mixture to a stress factor F of less than about 30 cm.sec$^{-1}$ where F is the product of the maximum shaking amplitude (peak to peak) and the shaking frequency. In contrast, mechanical stress to reduce aggregation/agglomeration by vigorous shaking will be at least 50 cm.sec$^{-1}$, preferably at least 80 cm.sec$^{-1}$. This can be achieved with vigorous manual shaking or alternatively using a vortex mixer or capmixer.

Where the reconstituted dispersion is subjected to mechanical stress by extrusion, this is preferably through at least one aperture or tube of diameter up to 1 mm (preferably 100 to 800 μm, e.g. a size 0.5 mm internal diameter, 40 mm length syringe needle), or more preferably through the pores of a filter. Where a filter is used, the pore size is preferably similar to or slightly smaller than the vesicle size, e.g. 1 to 10 μm, particular 3 to 6 μm, especially 5 μm. Such filters are available commercially as sterile devices for pharmaceutical and material use.

The passage of the vesicles through such filters results in very little change in the total vesicle content, the vesicle mean size and size distribution, or the echogenicity of the dispersion.

Where a filter is used, this may conveniently be in a filter device assembly.

Viewed from a further aspect therefore the invention provides a pharmaceutical composition kit comprising: (i) a filter device assembly; (ii) either a sterile aqueous dispersion of gas-containing amphiphile-membraned vesicles or a sterile aqueous reconstitution medium and separately a water-dispersible material containing gas-containing amphiphile-membraned vesicles; optionally (iii) a syringe body capable of being fitted with said filter device assembly; and optionally (iv) a needle for injection. The latter may be used for withdrawal of the dispersion if the filter device assembly of (i) is used for injection.

Advantageously, the kit of the invention contains a syringe body pre-filled with a sterile aqueous dispersion of the gas-containing vesicles.

The gas in the gas-containing vesicles in the processes and products of the invention may be any physiologically tolerable gas or gas mixture, by which is included materials which are gaseous at body temperature, e.g. 37° C. Suitable gases include air, oxygen, nitrogen, helium, carbon dioxide, sulphur hexafluoride, low molecular weight hydrocarbons and fluorinated low molecular weight hydrocarbons, and mixtures of two or more thereof. Particularly suitably the gas comprises a perfluorocarbon, e.g. perfluorobutane or perfluoropentane. Examples of other suitable gases may be found in WO-A-97/29783 (Nycomed), the full disclosures whereof are incorporated herein by reference.

The vesicle may be monolayered or multilayered, but preferably is substantially monolayered.

The vesicle membranes may be formed of any suitable amphiphilic membrane forming material, for example an ionic or nonionic surfactant, a protein or a phospholipid. Particularly preferably, the amphiphilic membrane forming material has a charged hydrophilic portion, in particular a negatively charged hydrophilic portion. Thus it is especially preferred that the membrane forming material be or at least include a charged phospholipid, for example a phosphatidyl serine. Again examples of suitable membrane forming materials may be found in WO-A-97/29783.

The gas-containing vesicles preferably have a median particle size by volume of 1 to 10 μm, especially 2 to 7 μm, particularly 2 to 5 μm and the volume concentration of microbubbles in the range of 7 to 10 μm is minimised. The gas-containing vesicles conveniently will be administered in concentrations of 0.1 to 50 μL/mL, especially 1 to 30 μL/mL, particularly 2 to 15 μL/mL, e.g. 10 μL/mL. As indicated above, the aqueous dispersion medium may contain further materials such as pH regulators, chelating agents, osmolality adjusters, stabilizing agents, etc. which may derive from the lyophilizate.

The present invention is especially applicable to compositions in which the gas in the gas-containing vesicle is perfluorobutane or perfluoropentane, the amphiphilic vesicle membrane-forming material is a phospholipid or a mixture of phospholipids, preferably phospholipids with an overall negative charge, such as phosphatidyl serine and phosphatidic acid, the median vesicle size (by volume) is 1–10 μm, and the vesicle concentration in ready-to-use form is 0.1 to 50 μL/mL.

The invention will now be described further with reference to the following non-limiting Examples.

EXAMPLE 1

A microbubble dispersion containing phosphatidyl serine stabilised perfluorobutane vesicles (prepared as described in Example 2(b) of WO-A-97/29783 (Nycomed), the full disclosures whereof are incorporated herein by reference) of 3±1 μm diameter (by volume) in a matrix of sucrose was diluted to a concentration of ½ and ¼ using a sucrose solution of 92 mg/ml. 2 ml samples of the resulting dispersion were taken, to which $CaCl_2$, $MgCl_2$ or $FeCl_2$ were added using 0.5 mM stock solutions. The final concentrations of the ions were 0.01–0.1 μM in increments of 0.01. With $FeCl_2$, additional concentrations of 0.12, 0.15 and 0.17 μM were tested to achieve agglomeration at the highest lipid concentration. pH in the final dilutions were typically 6.2. The vials were evaluated visually to determine whether or not any agglomerates were present immediately after addition of ions and after approximately 2 and 20 hours. The results are shown in FIG. 1.

Figure 1:
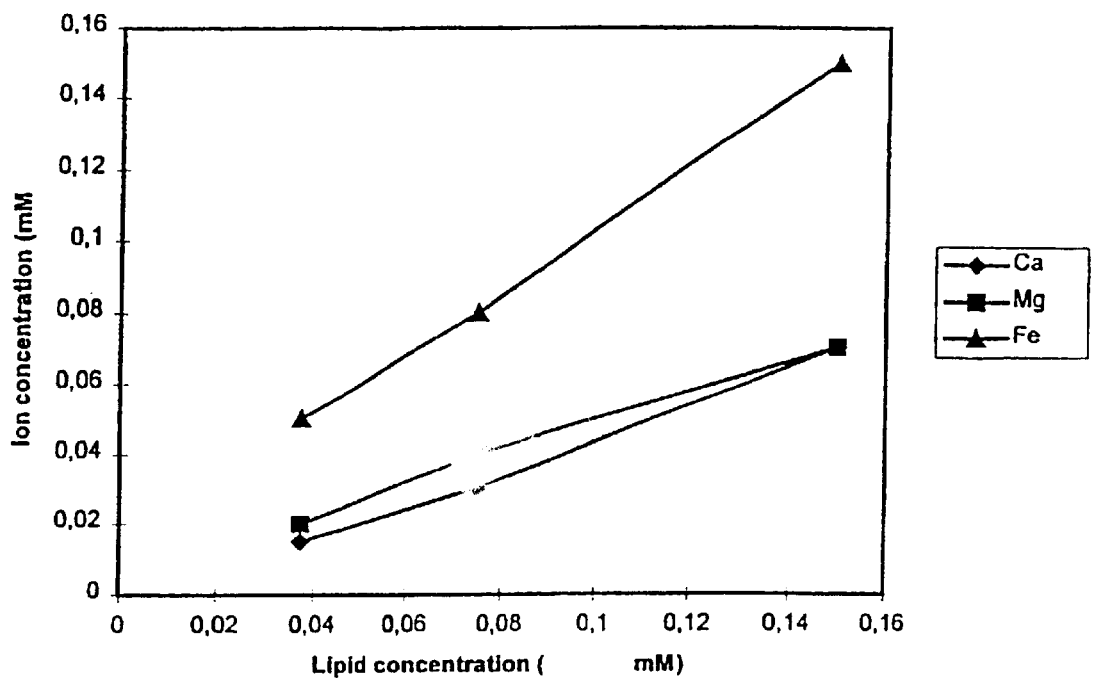
FIG. 1 shows the correlation between decreased phospholipid content and decreased cation tolerance achieved by diluting a dispersion of microbubbles to ½ and ¼.
Figure 2:
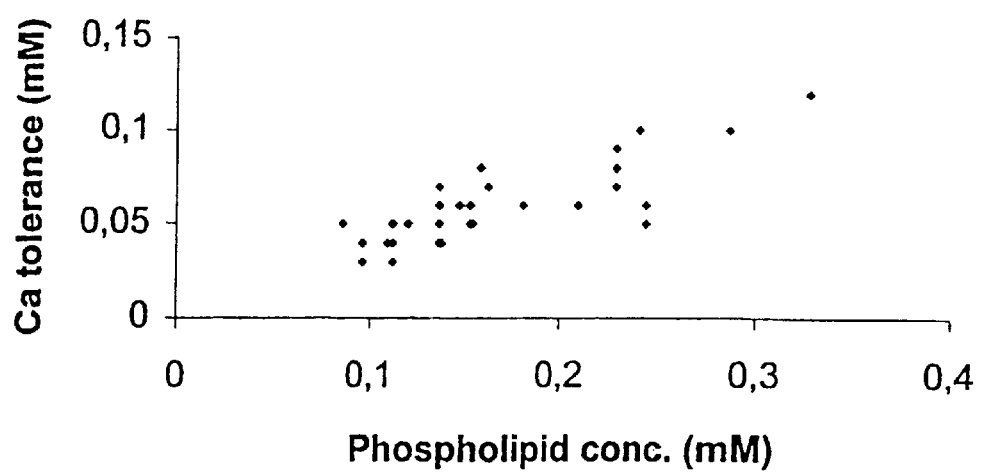
FIG. 2 shows how increased phospholipid content (by increase of available phospholipid surface incorporated or not incorporated in the microbubbles) prior to freeze-drying increases the calcium tolerance of the freeze-dried formulation.

FIG. 1 shows the lowest ion concentration that produced visible agglomeration after approximately 20 hours. The lowest ion concentration that produces visible or microscopic agglomeration is described as the "threshold". With Ca and Fe little change occurred from 1–20 hours after addition, whereas with Mg the lowest precipitating concentration decreased to the half during this time period. The end-point level is however similar for Ca and Mg, indicating the same mechanism of destabilisation for these two ions, but a different speed of reaction. Both ions precipitate the lipid when the ion:lipid mol ratio is more than 1:2. In contrast, Fe seems less reactive and precipitation occurs at a mole ratio of 1:1 and above. The thresholds at 20 hours were linearly correlated with the lipid concentration.

EXAMPLE 2

A lyophilizate containing phosphatidyl serine encapsulated perfluorobutane vesicles (prepared as described in Example 2(b) of WO-A-97/29783 (Nycomed), the full disclosures whereof are incorporated herein by reference) of 3±1 μm diameter (by volume) in a matrix of sucrose was dispersed in eleven 2 mL water (or diluent) samples to produce dispersions with a vesicle concentration of 10 μL/mL. The dispersions were examined visually to determine whether or not any agglomerates were present. The results of these examinations and the free metal ion concentrations of the water samples before reconstitution are set out in Table 1 below.

TABLE 1

Cation concentrations

| Water Sample No. | Al (μM) | Ba (μM) | Ca (μM) | Mg (μM) | Zn (μM) | Total* (μM) | Agglomerates observed |
|---|---|---|---|---|---|---|---|
| 1 | 9.51 | 0.208 | 8.46 | 72.2 | <0.2 | 90 | Yes |
| 2 | 5.73 | 0.200 | 7.76 | 107 | <0.2 | 121 | Yes |
| 3 | 6.05 | 0.183 | 10.8 | 94.6 | <0.2 | 112 | Yes |
| 4 | 8.89 | 0.200 | 7.55 | 73.6 | <0.2 | 90 | Yes |
| 5 | 5.96 | 1.01 | 2.64 | 6.3 | Trace | 16 | No |
| 6 | 5.40 | 0.908 | 3.02 | 7.1 | Trace | 16 | No |
| 7 | <0.7 | <0.03 | Trace | Trace | Trace | <1.4 | No |
| 8 | <0.7 | Trace | 8.51 | 1.3 | 33 | 43 | No |
| 9 | 2.58 | 0.146 | 6.19 | 37.3 | <0.2 | 46 | No |
| 10 | 6.25 | 0.292 | 10.9 | 157 | <0.2 | 174 | Yes |
| 11 | 5.06 | 0.265 | 8.54 | 125 | <0.2 | 139 | Yes |

(*Al, Ba, Ca, Mg and Zn)

Batches 5 and 6 were samples of sterile water from Kabi Pharmacia. Batch 8 was a sample of sterile water from B. Braun Medical AB. Batch 7 was a sample of freshly distilled water.

EXAMPLE 3

Kit

An ultrasound contrast agent kit is produced comprising a sterile packed filter needle having a 5μm rating; a prefilled sealed syringe containing 2 mL sterile water; a needle for injection; and a sealed vial containing a lyophilizate containing gas-containing vesicles as ed in Example 1 sufficient to produce, on reconstitution with the sterile water, a 10 μL/mL dispersion.

What is claimed is:

1. In a process for the preparation of a pharmaceutical composition comprising an aqueous dispersion of gas-containing vesicles having membranes comprising amphiphilic membrane-forming material, said material including at least one phospholipid having an overall negative charge, said process comprising:

(i) generating an aqueous dispersion of gas-containing vesicles from a mixture comprising said amphiphilic membrane-forming material; and (ii) lyophilizing said aqueous dispersion of gas-containing vesicles; and (iii) reconstituting the lyophilized product of step (ii) with a sterile aqueous liquid to produce an aqueous dispersion of gas-containing vesicles, the improvement comprising effecting said reconstitution in step (iii) with a sterile aqueous liquid such that the ratio of the total molar concentration in the aqueous dispersion of non-chelated Al, Ba, Mg, Ca and Zn ions to the molar concentration of said negatively charged phospholipid is less than 1:3.

2. The process of claim 1 wherein said ratio of the total molar concentration in the aqueous dispersion of non-chelated Al, Ba, Mg, Ca and Zn ions to the molar concentration of negatively charged phospholipid is less than 1:6.

3. The process of claim 1 wherein the total molar concentration in the aqueous dispersion of non-chelated Al, Ba, Ca, Mg, and Zn ions is less than 47 μM.

4. The process of claim 1 wherein said amphiphilic membrane-forming material includes at least one phosphatidylserine.

5. The process of claim 1 wherein the aqueous dispersion produced in step (i) is treated prior to step (ii) to increase the amount or the surface area of said amphiphilic membrane-forming material.

6. The process of claim 1 wherein the aqueous dispersion produced in step (i) is fractionated by flotation, filled into vials and then immediately frozen for lyophilisation in accordance with step (ii).

7. The process of claim 1 wherein the aqueous dispersion produced in step (i) is filtered and/or subjected to mechanical stress prior to step (ii).

8. The process of claim 1 wherein the reconstituted aqueous dispersion produced in step (iii) is filtered and/or subjected to mechanical stress prior to use.

9. The process of claim 1 wherein the sterile aqueous liquid employed in step (iii) is sterile water.

10. The process of claim 1 wherein the sterile aqueous liquid employed in step (iii) is sterile water containing one or more solutes selected from the group consisting of chelating agents, osmolality adjusting agents and pH regulators.

* * * * *